United States Patent [19]

Rafft et al.

[11] Patent Number: 4,762,704

[45] Date of Patent: Aug. 9, 1988

[54] ANTIPERSPIRANT COMPOSITIONS, CONTAINING CERTAIN ANTIHISTAMINES AND CERTAIN ANTIHISTAMINE ENHANCERS

[75] Inventors: Ronald R. Rafft, Towaco; Michael D. Helman, Edison, both of N.J.; Leonard Mackles, New York, N.Y.

[73] Assignee: Bristol-Myers Company, New York, N.Y.

[21] Appl. No.: 859,188

[22] Filed: Apr. 28, 1986

Related U.S. Application Data

[63] Continuation of Ser. No. 506,930, Jun. 22, 1983, abandoned.

[51] Int. Cl.[4] .......................... A61K 7/32; A61K 9/07; A61K 9/08; A61K 9/10
[52] U.S. Cl. .................................... 424/65; 514/828; 514/937; 514/969
[58] Field of Search .................... 424/65, 66, 67, 68

[56] References Cited

U.S. PATENT DOCUMENTS

| 3,304,230 | 2/1967 | Abramson et al. | 424/47 |
| 3,767,786 | 10/1973 | MacMillan | 424/66 |
| 3,896,238 | 7/1975 | Smith | 424/66 |
| 3,948,943 | 4/1976 | Eberhardt et al. | 424/65 |
| 3,963,833 | 6/1976 | De Salva et al. | 424/65 |
| 4,053,630 | 10/1977 | Yu et al. | 424/289 |
| 4,089,942 | 5/1978 | Bore et al. | 424/47 |
| 4,226,850 | 10/1980 | Packman et al. | 424/47 |
| 4,234,566 | 11/1980 | Packman et al. | 424/47 |

OTHER PUBLICATIONS

Goodall, J. Clin. Pharm., 1970, vol. 10 pp. 235–246.
Marzuli et al Advances in Modern Toxicology, 1977, vol. 4 Chapt. 1, pp. 2–15.
The Merck Index, 9th Edition, 1976, p. 4302.

*Primary Examiner*—Dale R. Ore
*Attorney, Agent, or Firm*—Morton S. Simon; Charles Zeller

[57] ABSTRACT

A topical antiperspirant composition containing an antihistamine selected from the group consisting of antazoline, pyrilamine, tripelennamine, diphenhydramine, phenindamine and their corresponding pharmaceutically acceptable salts and an enhancer for said antihistamine selected from the group consisting of sodium sulfate, glutamic acid; octyl palmitate and propylene glycol methyl ether.

24 Claims, No Drawings

ANTIPERSPIRANT COMPOSITIONS, CONTAINING CERTAIN ANTIHISTAMINES AND CERTAIN ANTIHISTAMINE ENHANCERS

This is a continuing application of application Ser. No. 506,930, filed on June 22, 1983, now abandoned.

This invention relates to topical antiperspirant compositions that make use of certain antihistamines. More particularly, it concerns compositions of this character that contain an enhancer for the antiperspirant activity of said antihistamines.

It has been suggested in the prior art to use certain antihistamines, alone or in combination with astringent metallic salts, as antiperspirant agents. This is exemplified by two U.S. Patents to Packman et al U.S. Pat. Nos. 4,226,850 and 4,234,566. In addition, in an article by Goodall published in the J. Clin. Pharm., Vol. 10, 1970, p. 235-246, it is suggested that certain anticholenergic or cholenergic blocking agents exhibit varying degrees of antiperspirant activity. Among the drugs that Goodall characterizes an anticholenergic drugs, he includes chlorpheniramine maleate, phenindamine tartrate, diphenhydramine HCl and tripelennamine HCl. A somewhat similar disclosure is to be found in "Advances in Modern Toxicology", Vol. 4, Dermatology and Pharmacology, Chapter 1, pages 2-25, edited by Francis N. Marzuli and Howard I. Maibach, published 1977, John Wiley & Sons, New York.

One thing that is quite clear from this prior art is that the vehicle from which these drugs are applied is important. The level of antiperspirant activity that these drugs exhibit is very much dependent upon the contents of the vehicle in which they are dispensed.

It has now been found that the antiperspirant activity of certain antihistamines may be enhanced by incorporating in a vehicle containing said antihistamine, an enhancer for said antihistamine described in more detail below.

It is accordingly an object of the present invention to provide an antiperspirant composition containing certain antihistamines as an active antiperspirant agent and also containing certain agents that enhance the antiperspirant activity of said antihistamines.

It is also an object of this invention to provide a process for inhibiting perspiration in a subject that makes use of the antiperspirant composition of the aforesaid object.

Other and more detailed objects of this invention will be apparent from the following description and claims.

In the practice of the present invention, it has been found that it is necessary to be quite selective in the antihistamine that is employed. For the purposes of this invention, a composition is an effective antiperspirant composition if it could be demonstrated to be at least weakly effective in the Rat Foot Pad Model described in more detail below without regard as to whether these results could be corroborated in clinical studies in human antiperspirant panels. The antihistamines that were found to be effective in accordance with the present invention are antazoline, pyrilamine, tripelennamine, diphenhydramine, phenindamine and their pharmaceutically acceptable salts. The type of salts of the aforesaid antihistamines that are useful for the purposes of this invention can vary. By way of example, the following may be mentioned: phosphates, maleates, hydrochlorides, succinates and tartrates.

The quantity of antihistamine that may be contained in the present compositions may vary somewhat depending on the vehicle utilized and the results that are desired. However, generally, this will be in the range of from about 1% to about 10% by weight based on the total weight of the composition; the preferred range being from about 3% to about 5% on the same weight basis.

As previously indicated, it is a feature of the present invention to incorporate in the instant antiperspirant compositions certain enhancers for the antiperspirant activity of the antihistamines employed. These also are quite selective and include sodium sulfate, glutamic acid (e.g. l-glutamic acid) octyl palmitate and propylene glycol methyl ether. The quantity of the antihistamine enhancers that will be present in these compositions may also vary somewhat. Usually, this will constitute between about 5% to about 95% by weight based on the total weight of the composition. Best results are obtained when the antiperspirant enhancer utilized falls within the range of from about 5% to about 30% by weight based on the total weight of the composition.

In accordance with the present invention, the antihistamine and the antihistamine enhancer will be distributed in a suitable vehicle which will generally be a liquid or fluid carrier. This will include solutions, suspensions, lotions, creams, ointments and the like. A variety of carriers may be employed but usually this will be an aqueous based carrier. By way of example, the following carriers may be mentioned: water, propylene glycol, ethanol, volatile silicones, ethoxylated ethers, isopropyl myristate and palmitate, etc.

In addition to the components mentioned above, the compositions of this invention may also contain those well known ingredients or adjuvants commonly found in antiperspirant compositions. These include such things as perfumes, coloring agents, stabilizers, buffers, thickeners, emulsifiers, etc.

The compositions of the present invention may be applied to a subject in the conventional manner to inhibit perspiration. Usually, this will involve applying to axillary vault of the subject a quantity of the composition sufficient to inhibit perspiration. This may vary depending upon the results desired, the concentration of the active ingredients and the vehicle employed. Generally, enough of the composition will be applied to deliver to the site from about 10 mgs to about 15 mgs of antihistamine per axilla.

The following Examples are given to further illustrate this invention. It is to be understood, however, that the invention is not limited thereto.

There is given in tabular form in Table I below Examples of the following invention in which the vehicle is primarily water in which the antihistamine and enhancer are dissolved.

TABLE I

| | % by Weight based on total wt. of composition | | | | | | | |
|---|---|---|---|---|---|---|---|---|
| | Ex 1 | Ex 2 | Ex 3 | Ex 4 | Ex 5 | Ex 6 | Ex 7 | Ex 8 |
| Antihistamine | | | | | | | | |
| (1) Antazoline phosphate | 5 | — | — | — | — | — | — | — |
| (2) Pyrilamine maleate | — | 5 | — | — | — | — | 5 | — |
| (3) Tripelennamine hydrochloride | — | — | 5 | — | — | — | — | — |

TABLE I-continued

| | % by Weight based on total wt. of composition | | | | | | | |
|---|---|---|---|---|---|---|---|---|
| | Ex 1 | Ex 2 | Ex 3 | Ex 4 | Ex 5 | Ex 6 | Ex 7 | Ex 8 |
| (4) Diphenhydramine hydrochloride | — | — | — | 5 | — | — | — | 5 |
| (5) Phenindamine tartrate | — | — | — | — | 5 | 5 | — | — |
| Enhancers | | | | | | | | |
| (6) Sodium sulfate | 20 | 20 | 20 | 20 | 20 | — | — | — |
| (7) l-glutamic acid | — | — | — | — | — | 20 | — | — |
| (8) DOWANOL PM* | — | — | — | — | — | — | 15 | — |
| (9) CERAPHYL 368** | — | — | — | — | — | — | — | 95 |
| Vehicle | | | | | | | | |
| (10) Water QS | 100 | 100 | 100 | 100 | 100 | 100 | 100 | — |

*Propylene glycol methyl ether
**Octyl palmitate

As indicated previously, the antiperspirant effectiveness of the compositions of the present invention were evaluated using the Rat Foot Pad Model. This procedure is discussed below.

RAT FOOT PAD MODEL

Materials and Methods

Female rats were utilized since they sweated more consistently than the male rats. Each material was evaluated in six Spraque Dawley rats (Taconic Farms, weight range 175–250 gm).

Three animals were injected (i.m.) in the right hind limb and three in the left hind limb (biceps femoris area) with 0.02 ml of Innovar Vet. This dose sedated the rats and facilitated placing them into polyethylene harnesses which were then fastened around each animal using binder clips. The harnessed rats were attached horizontally to supporting rods by wire hooks. In this manner, they were prevented from walking or licking their feet during the test.

Prior to treatment, the foot pads of both hind feet were swabbed with 70% alcohol to remove cellular debris. Treatment consisted of immersing the right hind foot into the test material for one minute. The foot was then allowed to air dry. The left hind foot served as an untreated control.

Observation of Sweat Inhibition/Rating

One hour post-treatment, both feet were swabbed with a 2% iodine in 95% alcohol solution which was permitted to air dry. The pads were then covered with a 50% mixture to starch in castor oil. When sweat was produced, it reacted with the "starch/iodine film" and was visible as a black spot at each pore. Sweating may occur spontaneously in rats or can be induced by an injection of 2% pilocarpine. Photos were taken for future evalution.

A material was considered effective (+) if all six rats exhibited 100% inhibition of the treated foot. A material which induced a marked decrease in the number of black dots per treated foot, was rated weakly effective (±). When a material did not differ from the untreated control, it was rated ineffective (−).

Using the above procedure, a series of antihistamines were tested in using the antihistamine enhancers of this invention. The results of these tests are summarized in Table II below:

TABLE II

| Antihistamines (5%) | 20%* Sodium Sulfate | 20%* l-Glutamic Acid | 15%* DOWANOL PM | 95%* CERAPHYL 368 |
|---|---|---|---|---|
| Antazoline phosphate | ± | | | |
| Pyrilamine maleate | + | | + | |
| Tripelennamine hydrochloride | + | | | |
| Diphenhydramine hydrochloride | ± | | | + |
| Doxylamine succinate | − | | | ± |
| Chlorpheniramine maleate | − | | | |
| Pheniramine maleate | − | | | |
| Phenindamine tartrate | + | + | | |

*Aqueous solutions

Although the invention has been described with reference to specific forms thereof, it will be understood that many changes and modifications may be made without departing from the spirit of this invention.

What is claimed is:

1. A topical antiperspirant comprising an active antiperspirant agent consisting essentially of an antihistamine distributed in a liquid vehicle containing an enhancer for the antiperspirant activity of said antihistamine,
    (a) said antihistamine being selected from the group consisting of, pyrilamine, tripelennamine, diphenhydramine, phenindamine and their corresponding pharmaceutically acceptable salts;
    (b) said antihistamine enhancer being selected from the group consisting of aqueous solutions of sodium sulfate, glutamic acid, octyl palmitate and propylene glycol methyl ether;
    (c) said antihistamine being present in said vehicle in sufficient concentration to inhibit perspiration;
    (d) said enhancer also being present in said vehicle at a concentration sufficient to enhance the antiperspirant effectiveness of said antihistamine; and
    (e) said enhancer selected for said composition being one that enhances the antiperspirant effectiveness of the antihistamine contained in said composition.

2. A topical antiperspirant composition comprising an active antiperspirant agent consisting essentially of an antihistamine distributed in a vehicle containing sodium sulfate as an enhancer for the antiperspirant activity of said antihistamine
    (a) said antihistamine being selected from the group consisting of pyrilamine, tripelenamine, phenindamine and their corresponding pharmaceutically acceptable salts;
    (b) said antihistamine being present in said vehicle in sufficient concentration to inhibit perspiration; and (c) said enhancer also being present in said vehicle at a concentration sufficient to enhance the antiperspirant effectiveness of said antihistamine.

3. A topical antiperspirant composition comprising an active antiperspirant agent consisting essentially of an antihistamine distributed in a vehicle containing glutamic acid as an enhancer for the antiperspirant activity of said antihistamine
   (a) said antihistamine being selected from the group consisting of phenindamine and its corresponding pharmaceutically acceptable salts;
   (b) said antihistamine being present in said vehicle in sufficient concentration to inhibit perspiration; and
   (c) said enhancer also being present in said vehicle at a concentration sufficient to enhance the antiperspirant effectiveness of said antihistamine.

4. An topical antiperspirant composition comprising an active antiperspirant agent consisting essentially of an antihistamine distributed in a vehicle containing propylene glycol methyl ether as an enhancer for the antiperspirant activity of said antihistamine
   (a) said antihistamine being selected from the group consisting of pyrilamine and its corresponding pharmaceutically acceptable salts;
   (b) said antihistamine being present in said vehicle in sufficient concentration to inhibit perspiration; and
   (c) said enhancer also being present in said vehicle at a concentration sufficient to enhance the antiperspirant effectiveness of said antihistamine.

5. A topical antiperspirant composition comprising an active antiperspirant agent consisting essentially of an antihistamine distributed in a vehicle containing octyl palmitate as an enhancer for the antiperspirant activity of said antihistamine
   (a) said antihistamine being selected from the group consisting of diphenhydramine and its corresponding pharmaceutically acceptable salts;
   (b) said antihistamine being present in said vehicle in sufficient concentration to inhibit perspiration; and
   (c) said enhancer also being present in said vehicle at a concentration sufficient to enhance the antiperspirant effectiveness of said antihistamine.

6. A composition according to claim 1 wherein said antihistamine enhancer is octyl palmitate and is present in said composition in a concentration of about 95% by weight based on the total weight of said composition.

7. A composition according to claim 1 in which said antihistamine is present in said composition in the range of from about 1% to about 10% by weight based on the total weight of said composition.

8. A composition according to claim 1 in which said antihistamine enhancer is present in said composition in the range of from about 5% to about 95% by weight based on the total weight of said composition.

9. A composition according to claim 1 in which said antihistamine is present in said composition in the range of from about 1% to about 10% by weight based on the total weight of said composition and said antihistamine enhancer is present in said composition in the range of from about 5% to about 95% based on the total weight of said composition.

10. A composition according to claim 1 in which said antihistamine is present in said composition in the range of from about 3% to about 5% by weight based on the total weight of said composition.

11. A composition according to claim 1 in which said antihistamine enhancer is present in said composition in the range of from about 5% to about 30% by weight based on the total weight of said composition.

12. A composition according to claim 1 in which said antihistamine is present in said composition in the range of from about 3% to about 5% by weight based on the total weight of said composition and said antihistamine enhancer is present in said composition in the range of from about 5% to about 30% by weight based on the total weight of said composition.

13. A composition according to claim 12 in which said antihistamine enhancer is sodium sulfate.

14. A composition according to claim 13 in which said antihistamine is pyrilamine maleate.

15. A composition according to claim 13 in which said antihistamine is tripelennamine hydrochloride.

16. A composition according to claim 13 in which said antihistamine is phenindamine tartrate.

17. A composition according to claim 12 in which said antihistamine enhancer is l-glutamic acid.

18. A composition according to claim 17 in which said antihistamine is phenindamine tartrate.

19. A composition according to claim 12 in which said antihistamine enhancer is propylene glycol methyl ether.

20. A composition according to claim 19 in which said antihistamine is pyrilamine maleate.

21. A composition according to claim 12 in which said antihistamine enhancer is octyl palmitate.

22. A composition according to claim 21 in which said antihistamine is diphenhydramine hydrochloride.

23. A process for inhibiting perspiration in a living subject which comprises applying to the skin of said subject an antiperspirant effective amount of the composition of claim 1, or 12.

24. A process for inhibiting perspiration in a living subject which comprises applying to the skin of said subject an antiperspirant amount of the composition of claim 6.

* * * * *